United States Patent [19]
Cox et al.

[11] Patent Number: 5,480,415
[45] Date of Patent: Jan. 2, 1996

[54] APPARATUS FOR HIGH SPEED DATA COMMUNICATION BETWEEN AN EXTERNAL MEDICAL DEVICE AND AN IMPLANTABLE MEDICAL DEVICE

[75] Inventors: Timothy J. Cox, Lake Jackson; Randolph K. Armstrong, Missouri City, both of Tex.

[73] Assignee: Intermedics, Inc., Angleton, Tex.

[21] Appl. No.: 437,514

[22] Filed: May 9, 1995

Related U.S. Application Data

[60] Continuation of Ser. No. 259,902, Jun. 15, 1994, abandoned, which is a division of Ser. No. 58,752, May 5, 1993, Pat. No. 5,383,912.

[51] Int. Cl.$^6$ .................................... A61N 1/37
[52] U.S. Cl. ........................................ 607/32
[58] Field of Search .................. 607/32, 33, 60, 607/61

[56] References Cited

U.S. PATENT DOCUMENTS

| | | | |
|---|---|---|---|
| 3,229,684 | 1/1966 | Nagumo et al. | 128/2 |
| 3,662,758 | 5/1972 | Glover | 605/61 |
| 4,041,954 | 8/1977 | Ohara | 128/419 PT |
| 4,155,470 | 9/1979 | Neumann | 607/33 |
| 4,172,459 | 10/1979 | Hepp | 128/697 |
| 4,187,854 | 2/1980 | Hepp et al. | 128/419 |
| 4,528,987 | 7/1985 | Slocum | 128/696 |
| 4,543,953 | 10/1985 | Slocum et al. | 607/32 |
| 4,561,443 | 12/1985 | Hogrefe et al. | 128/419 PG |
| 4,941,201 | 7/1990 | Davis | 455/41 |
| 4,980,898 | 12/1990 | Silvian | 607/32 |
| 5,117,825 | 6/1992 | Grevious | 607/32 |
| 5,342,408 | 8/1994 | deCoriolis et al. | 605/32 |

OTHER PUBLICATIONS

W. H. Ko et al., "Single Frequency RF Powered ECG Telemety System," IEEE Transactions on Biomedical Engineering, vol. BME–26, No. 2, Feb. 1979, USA, pp. 105–109.

D. F. Lovely et al., "Implantable Myoelectric Control System with Sensory Feedback," Medical and Biological Engineering and Computing, vol. 23, No. 1, Jan. 1985, Great Britain, pp. 87–89.

*Primary Examiner*—William E. Kamm
*Attorney, Agent, or Firm*—Richard L. Robinson

[57] ABSTRACT

A method of communicating data between an external device and an implantable medical device wherein a first pulse is transmitted as electromagnetic energy from one device to the other, is received and stored as electrostatic energy in the second device and, after a delay period representing data to be communicated, the stored energy is released and transmitted as electromagnetic energy back to the first device. A communications circuit in the implantable device for accomplishing the method includes an antenna coil, a non-linear electronic component in circuit communication with the antenna coil, a storage capacitor in circuit communication with the antenna coil and non-linear electronic component for storing energy received by the antenna coil, and a switch for selectively connecting the charged storage capacitor and the antenna coil to discharge the charge stored in the capacitor into the antenna coil.

15 Claims, 4 Drawing Sheets

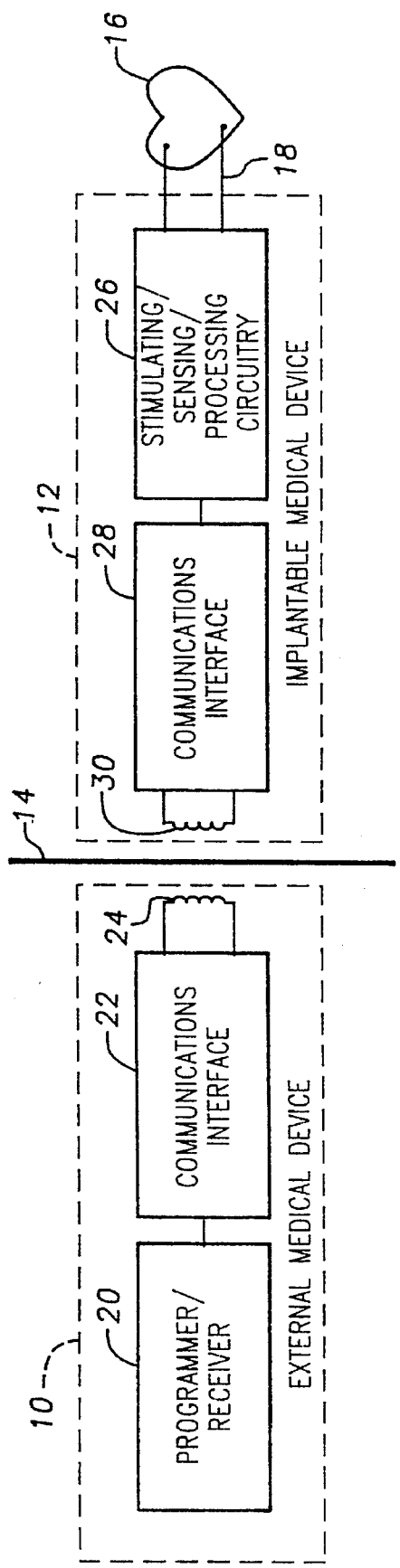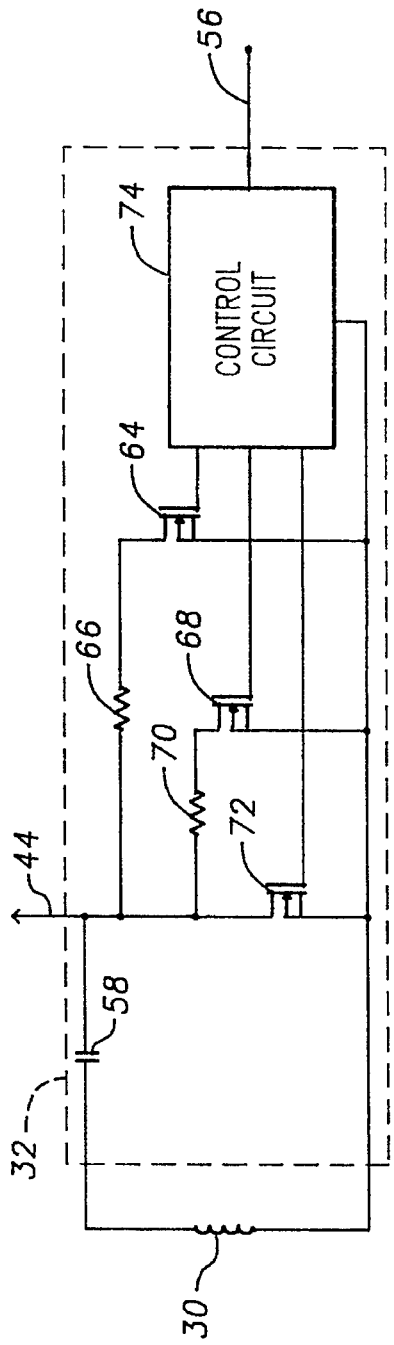
FIG. 1
FIG. 7

APPARATUS FOR HIGH SPEED DATA COMMUNICATION BETWEEN AN EXTERNAL MEDICAL DEVICE AND AN IMPLANTABLE MEDICAL DEVICE

This is a continuation of application Ser. No. 08/259,902 filed on Jun. 15, 1994, now abandoned which is a divisional of application Ser. No. 08/058,752, filed on May 5, 1993, now U.S. Pat. No. 5,383,912.

BACKGROUND OF THE INVENTION

1. Field of the Invention

This invention relates generally to implantable medical devices and relates more particularly to schemes for communicating data between external medical devices and implantable medical devices.

2. Background Information

Recent implantable medical devices such as cardiac stimulators, including pacemakers and defibrillators, are generally controlled by microprocessors. This permits a variety of modes and parameters of the device to be changed by the physician to customize the operation of the device to the patient's condition. Such devices also are capable of sensing a number of physiological parameters of the patient which would be of use to the physician. It is therefore necessary to provide means for communicating with the implantable medical device both prior to and after implantation in the patient. This is often accomplished with an external medical device such as a programmer which provides an appropriate interface to the physician in the form of display and input devices, and which provides a wand that can be placed in proximity to the implantable medical device to provide communication over a short distance.

The communication over distance can be provided by transmission of electromagnetic energy between the external and implantable devices. The information transmitted between the devices can be in the form of discrete pulses of energy that are modulated in such a way as to encode the data to be transferred.

Because it is necessary to maintain the wand of the programmer in proximity to the implantable medical device for the duration of communication, there is a practical limit to the amount of data that can be transmitted within a convenient amount of time. Naturally, the speed of data communications will have a great influence on the total amount of data communicated during a given amount of time. It is therefore desirable to provide a data encoding scheme that permits rapid transfer of data between the devices.

It is a general rule that as the speed of data communication increases, the power consumed to accomplish the communication also increases. This does not present a limitation in the case of the external medical device, since it can be energized from the power mains. In the case of the implantable medical device, however, which is powered by an internal battery, the increased power consumption occasioned by high speed communications can unduly limit the lifespan of the battery. It would therefore be desirable to provide a high speed data communication arrangement that shifts the burden of extra power consumption away from the implantable device to the external device.

SUMMARY OF THE INVENTION

It is an object of the invention to provide an apparatus and method for communicating data between an external medical device and an internal medical device that accomplishes the desirable objectives set forth above. Other objects and advantages of the invention will be apparent from the following descriptions and drawings of preferred embodiments of the invention.

In accordance with one aspect of the invention, a method of communicating data between an implantable medical device and an external device is provided, the method including the steps of transmitting a first pulse of electromagnetic energy from one of the implantable medical device and the external device, and receiving the first pulse of energy in the other of the implantable medical device and the external device. After a selected time delay following receipt of the first pulse of energy, where the time delay represents data to be communicated, a second pulse of electromagnetic energy is transmitted from the second device. The second pulse of energy is received in the first device.

In accordance with another aspect of the invention, a method of communicating data between an implantable medical device and an external device includes the steps of transmitting a first pulse of electromagnetic energy from the external device to the implantable medical device, receiving in the implantable medical device the first pulse of electromagnetic energy and storing the received energy, transmitting a second pulse of electromagnetic energy from the implantable medical device to the external device, wherein transmission of the second pulse is effected by releasing the stored energy, and receiving in the external device the second pulse of electromagnetic energy. Transmission of data from the implantable medical device to the external device is therefore powered by energy supplied by the external device.

In accordance with yet another aspect of the invention, a method of effecting simultaneous bi-directional data communication between an external device and an implantable medical device includes the steps of transmitting a first train of pulses of electromagnetic energy from one to the other of the external device and the implantable medical device, and transmitting a second train of pulses of electromagnetic energy from the other to the one of the external device and the implantable medical device, wherein each pulse of at least one of the first and second trains of pulses is interleaved in time between adjacent pulses of the other train of pulses.

in accordance with still another aspect of the invention, an implantable medical device is provided for use with an external device that transmits discrete pulses of electromagnetic energy to the implantable medical device. The implantable medical device has a communication circuit for communicating data from the implantable medical device to the external device that includes an antenna coil configured to receive a first pulse of electromagnetic energy transmitted from the external device and thereby to have produced therein a first transient electric current, and also configured to receive therein a second transient electric current and thereby to radiate a second pulse of electromagnetic energy to the external device. A non-linear electronic component is provided in circuit communication with the antenna coil to convert the first transient electric current into a non-zero average electric current. A storage capacitor is provided in circuit communication with the antenna coil and the non-linear electronic component and is charged by the non-zero average electric current. A switch in circuit communication with the storage capacitor and the antenna coil is provided for selectively connecting the charged storage capacitor and the antenna coil in circuit communication such that the charge stored in the storage capacitor is discharged into the antenna coil as the second transient electric current. Controller circuitry is provided for selectively closing the switch after a selected time delay following receipt of the first pulse of electromagnetic energy, the selected time delay representing data to be communicated. Transmission of data from the implantable medical device to the external device is powered by energy supplied by the external device.

BRIEF DESCRIPTION OF THE DRAWINGS

FIG. 1 is a block diagram of an external medical device and an implantable medical device in accordance with the present invention.

FIG. 7 is still another alternate embodiment of the energy capture, storage and release circuit of the communications interface of FIG. 2, providing for pulse shaping of the transmitted pulse.

DETAILED DESCRIPTION OF THE PREFERRED EMBODIMENT

Figure 2:
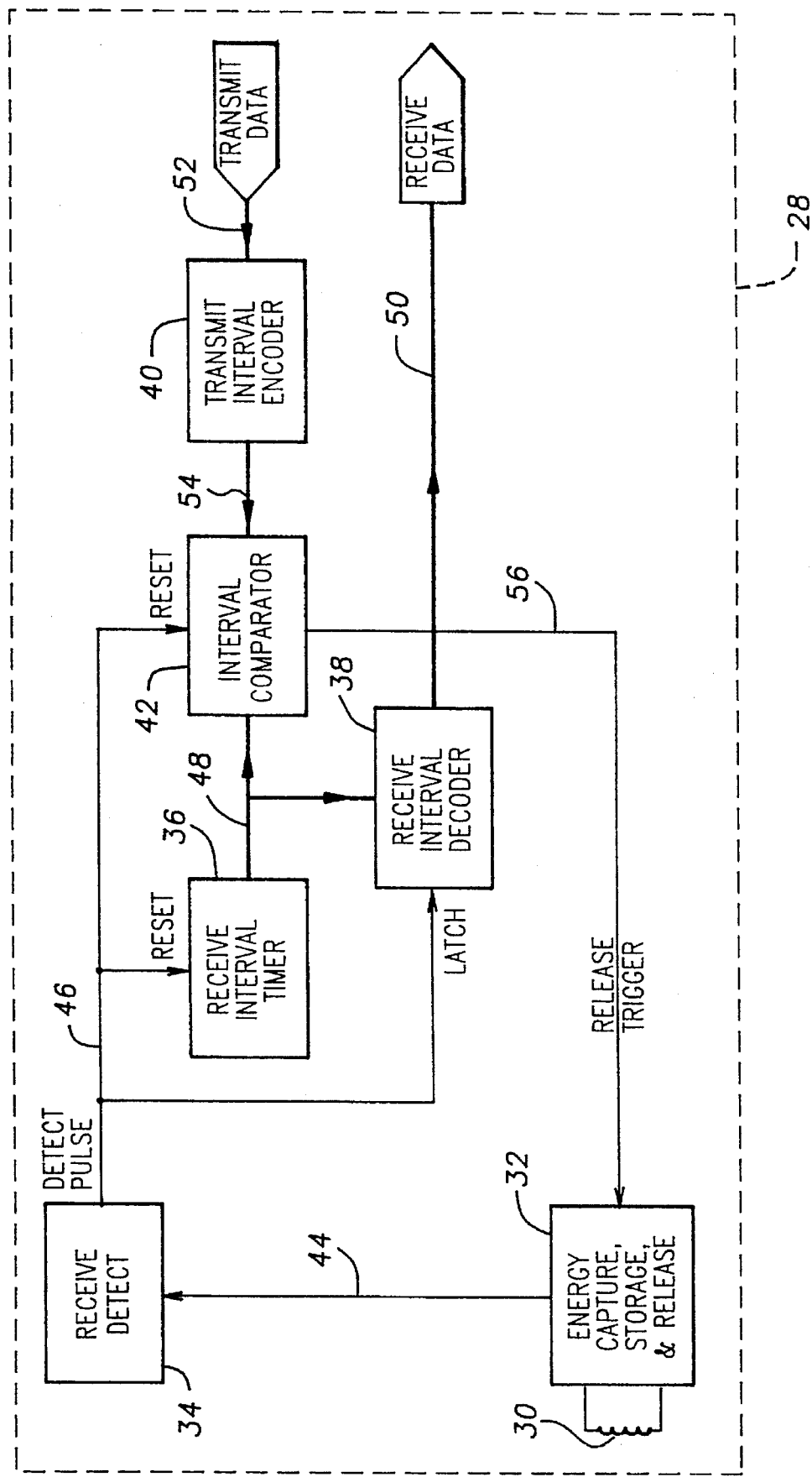
FIG. 2 is a block diagram of the communications interface of the implantable medical device of FIG. 1.

Referring particularly to FIG. 1, there is illustrated a block diagram of a system for artificial cardiac stimulation. The system includes an external medical device 10 and an implantable medical device 12 that are ordinarily physically separated in use by a barrier 14 representing the surface of the human body. External device 10 is a programmer that is located externally of the human body and is configured and arranged to issue commands to and receive information from implantable device 12 via electromagnetic telemetry. Implantable device 12 is a cardiac stimulator such as a pacemaker or defibrillator that is ultimately implanted in the human body in electrical communication with the heart 16 via one or more electrical leads and electrodes 18. During ordinary operation of implantable device 12, which is powered by a self-contained battery, device 12 operates under its own control and is not in proximity to external device 10. When implantable device 12 is first implanted, however, and periodically thereafter, it is necessary to communicate with implanted device 12 to issue programming commands to change operating modes or parameters, or to collect physiological or operational information sensed by implantable device 12. Therefore, from time to time, external device 10 is placed in proximity to implantable device 12 and communication is commenced via electromagnetic telemetry.

External device 10 can be understood as comprising a programmer/receiver portion 20, including a user interface such as an input device and/or a display screen, and a communications interface 22 including an antenna coil 24. Similarly, implantable device 12 can be understood as comprising stimulating/sensing/processing circuitry 26 in electrical communication with heart 16 via leads 18, and a communications interface 28 including an antenna coil 30. Antenna coil 24 of external device 10 can be located in a wand that can be placed over the implantable device 12 in relatively close proximity thereto, both before and after implantation.

Referring now to FIG. 2, there is illustrated a block diagram of communications interface 28 of the implantable medical device 12. It should be understood that communications interface 28 sends and receives data between itself and the communications interface 22 of external device 10 via pulses of electromagnetic energy. Communications interface 28 is also in circuit communication with additional circuitry of the implantable device, designated generally as stimulating/sensing/processing circuitry 26 in FIG. 1, and sends and receives data between itself and the additional circuitry as binary data.

Communications interface 28 includes an antenna coil 30 and a number of related circuits, including energy capture, storage and release circuit 32, receive detect circuit 34, receive interval timer 36, receive interval decoder 38, transmit interval encoder 40 and interval comparator 42.

Considering first the reception of data by communications interface 28, data is communicated from external device 10 to implantable medical device 12 by pulses of electromagnetic energy that are transmitted from antenna coil 24 operably connected to external device 10. The pulses of electromagnetic energy are received in the implantable medical device by antenna coil 30, whereupon the energy received is captured, stored, and ultimately released again by capture circuit 32 to be retransmitted by antenna coil 30. The storage and retransmission feature is explained further below with respect to the transmission of data by communications interface 28. Capture circuit 32 has an analog output connected to line 44, which is connected to an input of receive detect circuit 34. Whenever a pulse of electromagnetic energy is received by capture circuit 32 through antenna coil 30, receive detect circuit 34 detects the event through line 44. Receive detect circuit 34 has an output connected to 1-bit digital line 46, which is connected to inputs of receive interval timer 36 and receive interval decoder 38. Upon detection of an electromagnetic pulse receive event, receive detect circuit 34 generates a detect pulse on line 46 which resets receive interval timer 36 and latches receive interval decoder 38. Receive interval timer 36 has an output connected to parallel data bus 48, which is connected to an input of receive interval decoder 38. Receive interval timer 36 outputs a cumulative timing count on bus 48, which is received by receive interval decoder 38. The timing count is decoded by receive interval decoder 38 and latched to receive data bus 50 when receive interval decoder 38 receives a detect pulse on 1-bit line 46. The interval is outputed to data bus 50 as 4 bits of binary data that is representative of the interval between the last two electromagnetic pulses received at antenna coil 30. in the preferred encoding scheme, the received data may be understood as a train of pulses wherein each pulse is pulse-position modulated relative to the next preceding pulse. Each received pulse represents binary data that is encoded in the time interval since receipt of the preceding pulse. For example, the time interval between successive pulses might be any one of 16 possible defined intervals. The shortest defined interval would be interpreted as decimal 0, or binary 0000 in a 4-bit nibble, and the longest defined interval would be interpreted as decimal 15, or binary 1111 in a 4-bit nibble. Receive interval decoder 38 converts the time interval, in the form of a clock cycle count, to a 4-bit binary output on bus 50. The received data in binary format may then be processed further by the stimulating/sensing/processing circuitry 26 of the implantable medical device to, for example, reprogram the parameters and modes of a pacemaker.

Considering next the transmission of data from implantable medical device 12 to external medical device 10, it should first be appreciated that in the preferred embodiment illustrated in FIG. 2, the electromagnetic energy that is transmitted from communications interface 28 does not have its source in the battery of the implantable medical device, but in the previously received and stored electromagnetic energy from the external device. Binary digital data from the implanted device is encoded as a time interval, and that time interval is used to trigger the release of stored energy for retransmission back to the external device. Viewed from another perspective, individual pulses of electromagnetic energy that are received by antenna coil 30 are captured and stored as electrostatic energy in capture circuit 32. After a selected delay following receipt of the pulse, which delay is representative of the information to be transmitted from the implantable medical device 12 to the external medical device, the stored electrostatic energy is released and converted back to electromagnetic energy that is transmitted from antenna coil 30. Thus, simultaneous bi-directional relative pulse-position modulation is obtained. In the preferred embodiment, pulses from the external device are position-modulated in time relative to the preceding pulse from the external device. Re-transmitted pulses from the implantable device are also position-modulated in time relative to the preceding pulse from the external device.

With particular reference to FIGS. 1 and 2, data to be transmitted by the implantable device 12 is communicated from stimulating/sensing/processing circuitry 26 as 4-bit binary data on bus 52 to the input of transmit interval encoder 40, which encodes the data as a timing count and outputs the timing count on bus 54. Interval comparator 42 receives the encoded timing count from bus 54 at one input, and receives the timing count from receive interval timer 36 on bus 48 at a second input, and compares the two inputs. When the timing count from interval timer 36 is equal to the encoded timing count from transmit interval encoder 40, interval comparator 42 generates a release trigger pulse on line 56. Energy capture, storage and release circuit 32 receives the release trigger pulse on line 56 and causes the energy from the previous received pulse to be released as electromagnetic energy from antenna coil 30.

Figure 3:
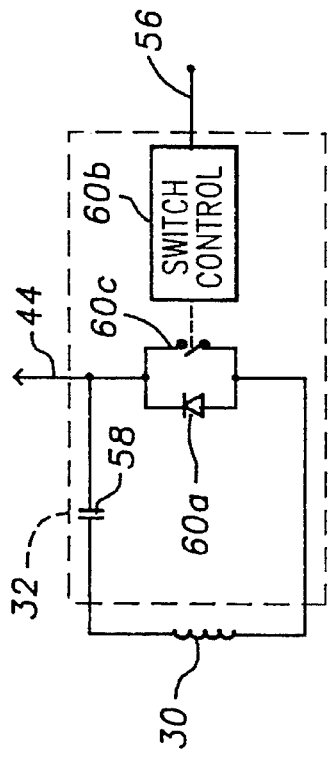
FIG. 3 is a schematic diagram of one embodiment of the energy capture, storage and release circuit of the communications interface of FIG. 2.

With particular reference to FIG. 3, energy capture, storage and release circuit 32 is shown in greater detail. Circuit 32 includes a storage capacitor 56 having one terminal connected to one end of antenna coil 30 and having the other terminal connected to the drain of a three-terminal electronic component, particularly a MOSFET transistor 60. The other end of antenna coil 30 is connected to the source of MOSFET 60. Line 56 from interval comparator 42 is connected to the gate of MOSFET 60. Due to the inherent diode characteristics between the source and drain of MOSFET 60 when in an off state, MOSFET 60 acts as a non-linear electronic component to convert transient electric current produced in antenna coil 30 by reception of electromagnetic energy to a non-zero average electric current which charges capacitor 58. Thus, an electromagnetic pulse transmitted by the external device 10 and received by antenna coil 30 is converted to electrostatic energy and stored in capacitor 56. The reception of the electromagnetic pulse is sensed by receive detect circuit 34 via line 44 connected to the junction of capacitor 58 and MOSFET 60. Alternatively, line 44 can be connected to the junction of capacitor 58 and antenna coil 30. Upon receipt of the release trigger pulse on line 56 at the gate of MOSFET 60, MOSFET 60 acts as a switch that is momentarily turned on so as to conduct between its source and drain terminals, whereupon the charge in capacitor 58 is discharged through antenna coil 30, generating a transient electric current in antenna coil 30 which is converted to electromagnetic energy and radiated from coil 30.

Figure 4:
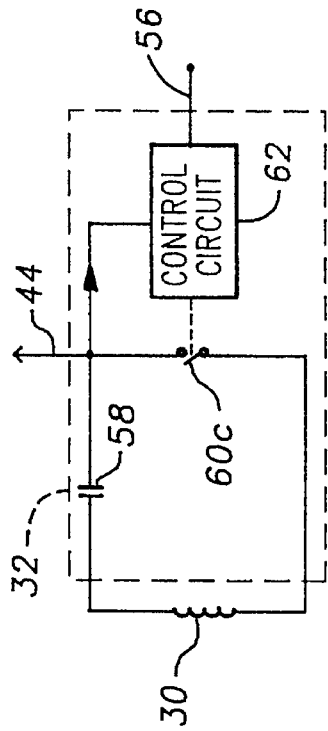
FIG. 4 is a schematic diagram of another embodiment of the energy capture, storage and release circuit of the communications interface of FIG. 2.

Referring to FIG. 4, there is illustrated a more generalized embodiment of the energy capture, storage and release circuit 32 in which the non-linear component 60a (shown here as a diode) for converting the transient electric current into a non-zero average electric current is separate from and in parallel with the switch component designated by switch control 60b and switch contacts 60c. It should be understood that switch control 60b and switch contacts 60c are representative of any conventional switch means for closing the circuit that can be controlled by a trigger release signal on line 56.

Figure 5:
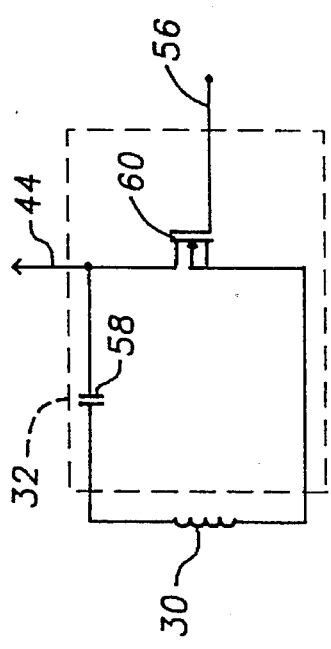
FIG. 5 is a schematic diagram of an alternate embodiment of the energy capture, storage and release circuit of the communications interface of FIG. 2.

Referring to FIG. 5, there is illustrated another alternative embodiment of circuit 32 in which antenna coil 30 is provided as a separate receiving coil 30a and a transmitting coil 30b. The non-linear component 60a is located in circuit communication between receiving antenna coil 30a and capadtor 58, whereas the switch designated by switch control 60b and switch contacts 60c is located in circuit communication between capacitor 58 and transmitting antenna coil 30b. It should be noted that transient electric currents in coil 30a charge capacitor 58 through the action of non-linear component 60a, illustrated as a diode, when switch contacts 60c are open. When switch contacts 60c are closed, capacitor 58 is discharged through transmitting antenna coil 30b.

Figure 6:
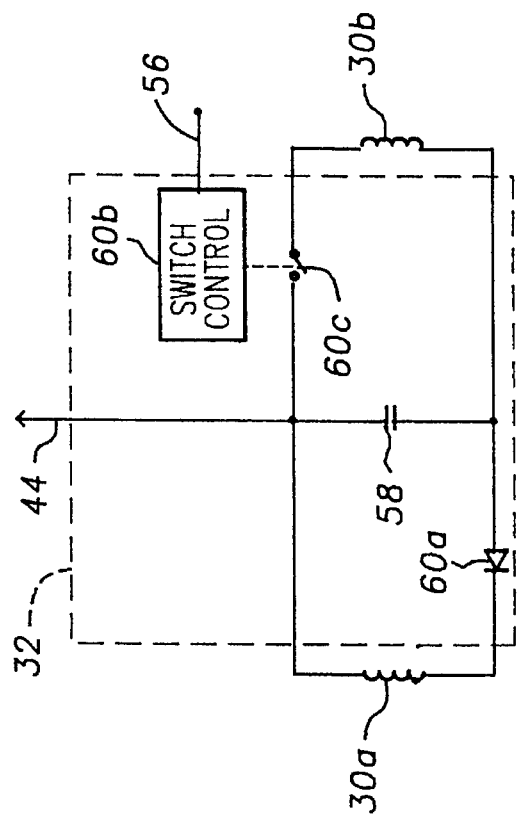
FIG. 6 is a schematic diagram of yet another alternate embodiment of the energy capture, storage and release circuit of the communications interface of FIG. 2.

Referring to FIG. 6, there is illustrated yet another alternative embodiment of circuit 32, in which the conversion of the transient electric current in antenna coil 30 into a non-zero average electric current for charging capacitor 58 is accomplished by opening switch 60c in synchronism with a voltage peak of the transient electric current as sensed by control circuit 62. Control circuit 62 then closes switch 60c to release the stored energy upon receipt of a trigger release signal on line 56.

It should be noted that the reception of communication pulses from an implantable medical device in an external medical device is often subject to interference, such as computer monitor emissions and inductive-loop hospital communicators. It is desirable to filter the received signal in order to improve discrimination from interference. However, the process of filtering may distort the wanted communication pulse in such a way as to degrade the following detection process. As the speed of communication increases, the problem is exacerbated. It is therefore useful to shape the communication pulse at transmission to compensate for the effects of the filter in the receiver. Referring to FIG. 7, there is illustrated an alternative embodiment of circuit 32 that accomplishes pulse shaping by using sequentially switched-on MOSFETS in place of the single MOSFET switch of FIG. 3. MOSFETS 64 and 68 are placed in parallel with MOSFET 72 in circuit communication between capacitor 58 and antenna coil 30, through respective resistors 66 and 70. Control circuit 74, upon receipt of a release trigger signal on line 58, causes MOSFET switches 64, 68 and 72 to be closed in that order at spaced time intervals. Resistors 68 and 70 are selected such that antenna coil 30 is first excited with a small packet of energy through MOSFET 64, followed by a larger packet through MOSFET 68, and finally by the largest packet of energy through MOSFET 72, the latter causing the largest amplitude voltage across antenna coil 30. It should be appreciated that the resistors 66 and 70 can be eliminated such that the drain terminals of both MOSFETS 64 and 68 are in circuit communication with capacitor 58, line 44 and the drain of MOSFET 72. In that case MOSFETS 64 and 68 would be selected to exhibit on-state channel resistances corresponding to the values of eliminated resistors 66 and 70, respectively.

Figure 8:
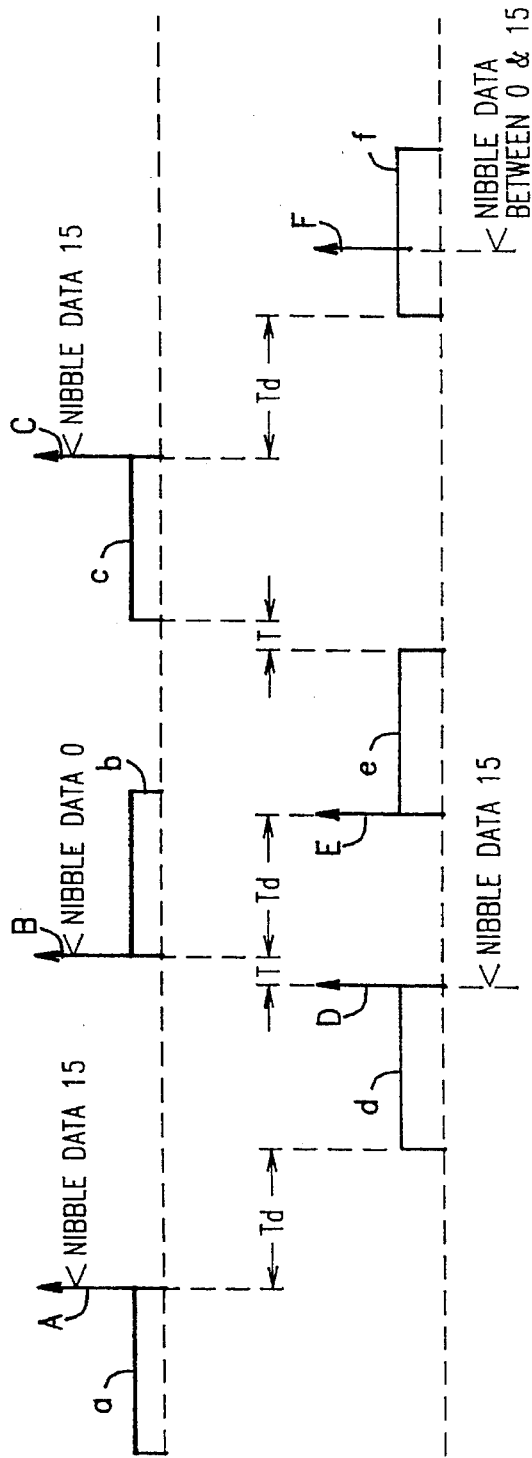
FIG. 8 is a timing diagram of a data modulating method in accordance with the present invention.

While the method of data encoding utilized in connection with the present invention has been described generally above in connection with the circuitry of the preferred embodiment, the encoding scheme may be better understood with reference to the timing diagram of FIG. 8. In that diagram, the top time line indicates a first train of pulses A, B and C received from the external medical device 10. The bottom time line indicates a second train of pulses D, E and F, with each pulse interleaved between successive received pulses A, B and C. Pulses D, E and F are transmitted by the implantable medical device 12. Associated with each pulse A, B and C is a respective time window a, b, and c. A pulse, such as pulse B, received at the beginning of its respective time window b, represents the first of 16 possible time positions within window b, and may be thought of as the relative pulse position modulation of the decimal number 0, or binary 0000 in a 4-bit nibble. A pulse, such as pulses A or C, received at the end of its respective time window a or c, represents the last of 16 possible time positions within windows a or c, respectively, and may be thought of as the relative pulse position modulation of decimal number 15, or binary 1111 in a 4-bit nibble. The time interval between pulses A and B, or between data 15 followed by data 0, is the minimum possible interval between successive received pulses. The time interval between pulses B and C, or between data 0 followed by data 15, is the maximum possible interval between successive received pulses. Following receipt of pulse A from the external medical device 10, a fixed time delay Td marks the beginning of the window d for transmission of pulse D from implantable medical device 12. Td represents the settling time required for the external medical device 10 following transmission of a pulse before the receive circuitry of the external device 10 will be able to sense a received pulse. In an ideal circuit, or if separate non-interacting isolated transmitters and receivers were employed, Td would be reduced to zero. As shown, pulse D is transmitted by the implantable medical device 12 at the end of its respective time window d, representing data 15. A small time delay T following the end of time window d is provided to permit reception and processing of pulse D in the external medical device before the next pulse B needs to be transmitted. In an ideal circuit time delay T would be reduced to zero. It can be seen that pulse D is pulse position modulated relative to pulse A in that D occurs in one of 16 positions in window d following a fixed delay interval Td. in the next cycle, pulse E is transmitted at the minimum delay interval Td following reception of pulse B, thereby occurring at the beginning of the respective time window e and representing data 0. In the last cycle illustrated, pulse F is transmitted after the minimum delay interval Td following pulse C but before the end of the respective time window f, thereby occurring in the middle of the time window f and representing a data value between 0 and 15. It can be seen that pulses E and F are each pulse position modulated relative to the next preceding received pulse, B and C, respectively, in that E and F each occur in one of 16 possible positions within respective time window e and f following a fixed delay interval Td. It should be understood that in this embodiment, each pulse of the second train of pulses is pulse position modulated relative to a preceding pulse of the first train of pulses. Thus, both B and D are positioned relative to A, and both C and E are positioned relative to B. C is positioned relative to B, and F is positioned relative to C.

As noted above, the scheme illustrated in FIG. 8 involves relative pulse position modulation of both the received and re-transmitted trains of pulses. However, in both trains of pulses, the modulated position of each pulse is relative to the next preceding pulse of only one of the trains of pulses. For example, in FIG. 8, pulse C of the first train and pulse E of the second train are both positioned relative to pulse B of the first train. The result of that scheme is that window c of the first train cannot begin until after the end of window e of the second train since pulse E can occur anywhere within window e. This results in an unnecessary delay between pulses B and C when pulse E is issued early in its time window e.

Figure 9:
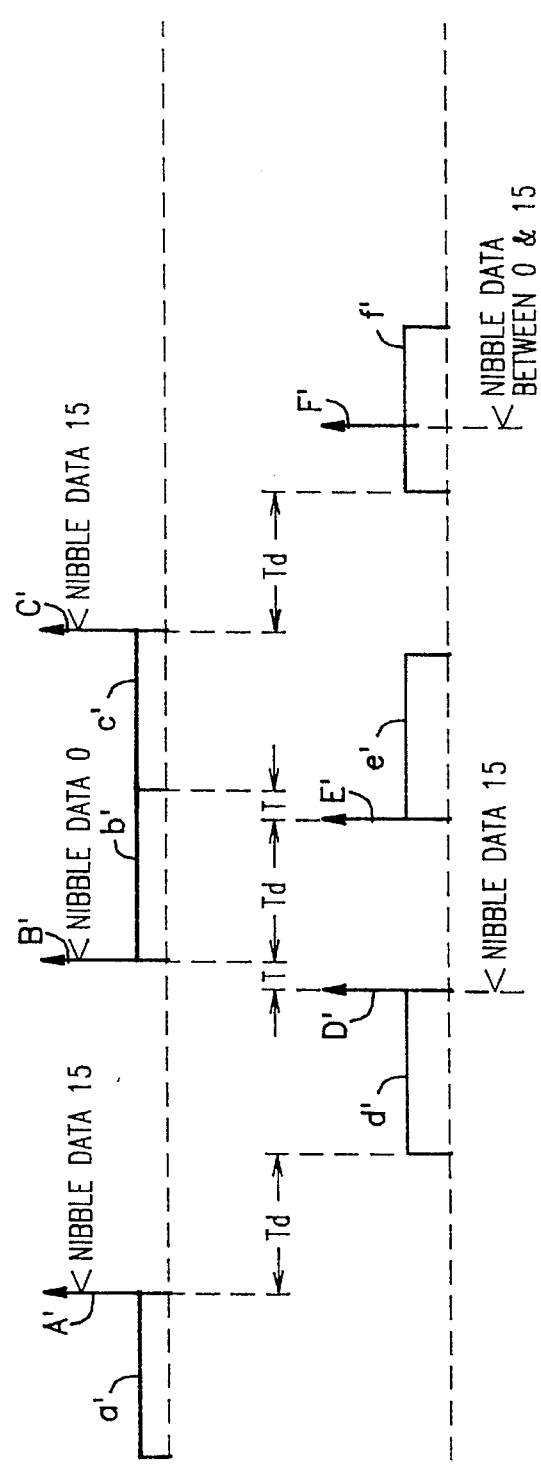
FIG. 9 is a timing diagram of an alternate data modulating method in accordance with the present invention.

Referring now to FIG. 9, an alternative encoding scheme is illustrated which results in greater biodirectional data density than the scheme illustrated in FIG. 8. For the sake of comparison between the encoding schemes of FIGS. 8 and 9, the pulses and time windows in FIG. 9 are indicated by like primed reference letters. In the alternative scheme, each pulse of each train of pulses is positioned relative to the immediately preceding pulse of the other train of pulses. For example, pulse C' is now positioned relative to pulse E' rather than relative to pulse B'. In the example shown, pulse E' occurs early in its time window e', thereby permitting the next time window c' to begin after a short delay T measured from pulse E' rather than from the end of time window e'. This has the effect of minimizing the time between successive pulses in each train.

While the present invention has been described in terms of preferred embodiments as shown in the drawings, the scope of the invention is not limited to such embodiments but only by the terms of the claims appended below.

What is claimed is:

1. In an implantable medical device of the type having means for generating data to be communicated to an external device, for use with an external device that transmits discrete pulses of electromagnetic energy to the implantable medical device, the improvement comprising a communication circuit for communicating data from the implantable medical device to the external device including:

antenna coil means for receiving a first pulse of electromagnetic energy transmitted from the external device such that a first transient electric current is produced therein, and also for receiving therein a second transient electric current such that a second pulse of electromagnetic energy is radiated therefrom to the external device;

non-linear means, in circuit communication with said antenna coil means, for converting the first transient electric current into a non-zero average electric current;

a storage capacitor in circuit communication with said antenna coil means and said non-linear means and charged by the non-zero average electric current;

switch means, in circuit communication with said storage capacitor and said antenna coil means, for selectively connecting the charged storage capacitor and said antenna coil means in circuit communication such that the charge stored in the storage capacitor is discharged into the antenna coil means as the second transient electric current; and controller means, in circuit communication with said means for generating data, said antenna coil means, and said switch means, and responsive to said data and said received first pulse of electromagnetic energy, for selectively actuating said switch means after a selected time delay following receipt of the first pulse of electromagnetic energy, the selected time delay having a duration representing data to be communicated;

wherein transmission of data from the implantable medical device to the external device is powered by energy supplied by the external device.

2. The implantable medical device of claim 1, in which said switch means comprises a plurality of switches in parallel with one another, said controller means including means for selectively actuating each of said plurality of switches sequentially.

3. The implantable medical device of claim 1, in which said switch comprises a three-terminal semiconductor, each terminal being in circuit communication with a respective one of said storage capacitor, said antenna coil means, and said controller means.

4. The implantable medical device of claim 3, in which said three-terminal semiconductor comprises a transistor.

5. The implantable medical device of claim 4, in which said transistor is a MOSFET.

6. The implantable medical device of claim 5, in which said MOSFET includes said non-linear means.

7. The implantable medical device of claim 1, in which said controller means includes receive detection means having an input in circuit communication with said antenna coil means for detecting receipt of a transmission pulse from the external device.

8. The implantable medical device of claim 7, in which said receive detection means further includes means for outputting a detect pulse in response to detection of a transmission pulse, and said controller means further includes transmit interval encoder means, having an input connected to the output of the receive detection means, for timing the elapsed time since the previous detect pulse and outputting a release trigger signal to said switch means at an elapsed time corresponding to a data value to be transmitted.

9. In an implantable medical device of the type having means for generating data to be communicated to an external device, for use with an external device that transmits discrete pulses of electromagnetic energy to the implantable medical device, the improvement comprising a communication circuit for communicating data from the implantable medical device to the external device including:

receiving antenna coil means for receiving a first pulse of electromagnetic energy transmitted from the external device such that a first transient electric current is produced therein;

transmitting antenna coil means for receiving therein a second transient electric current such that a second pulse of electromagnetic energy is radiated therefrom to the external device;

non-linear means, in circuit communication with said receiving antenna coil means, for converting the first transient electric current into a non-zero average electric current;

a storage capacitor in circuit communication with said receiving antenna coil means and said non-linear means and charged by the non-zero average electric current;

switch means, in circuit communication with said storage capacitor and said transmitting antenna coil means, for selectively connecting the charged storage capacitor and said transmitting antenna coil means in circuit communication such that the charge stored in the storage capacitor is discharged into the transmitting antenna coil means as the second transient electric current; and controller means, in circuit communication with said means for generating data, said receiving antenna coil means, said transmitting antenna coil means, and said switch means, and responsive to said data and said received first pulse of electromagnetic energy, for selectively actuating said switch means after a selected time delay following receipt of the first pulse of electromagnetic energy, the selected time delay having a duration representing data to be communicated;

wherein transmission of data from the implantable medical device to the external device is powered by energy supplied by the external device.

10. The implantable medical device of claim 9, in which said switch means comprises a three-terminal semiconductor, each terminal being in circuit communication with a respective one of said storage capacitor, said transmitting antenna coil means, and said controller means.

11. The implantable medical device of claim 10, in which the three-terminal semiconductor comprises a transistor.

12. The implantable medical device of claim 11, in which said transistor is a MOSFET.

13. The implantable medical device of claim 12, in which said MOSFET includes said non-linear means.

14. The implantable medical device of claim 9, in which said controller means includes receive detection means having an input in circuit communication with said receiving antenna coil means for detecting receipt of a transmission pulse from the external device.

15. The implantable medical device of claim 14, in which said receive detection means further includes means for outputting a detect pulse in response to detection of a transmission pulse, and said controller means further includes transmit interval encoder means, having an input connected to the output of the receive detection means, for timing the elapsed time since the previous detect pulse and outputting a control signal to said switch means at an elapsed time corresponding to a data value to be transmitted.

* * * * *